United States Patent [19]

Schulte et al.

[11] Patent Number: 5,188,937
[45] Date of Patent: Feb. 23, 1993

[54] LAYERED SANDWICH ASSAY METHOD FOR CHLAMYDIA AND MATERIALS THEREFOR

[75] Inventors: Thomas H. Schulte, Cary; Stewart R. Jurgensen; James P. Mapes, both of Raleigh, all of N.C.

[73] Assignee: Becton, Dickinson and Company, Franklin Lakes, N.J.

[21] Appl. No.: 733,070

[22] Filed: Jul. 17, 1991

Related U.S. Application Data

[63] Continuation of Ser. No. 334,255, Apr. 6, 1989, abandoned.

[51] Int. Cl.$^5$ .................. G01N 33/571; G01N 33/543
[52] U.S. Cl. .................................. 435/7.36; 435/7.91; 435/7.94; 435/18; 435/19; 435/21; 435/24; 435/975; 436/518; 436/532
[58] Field of Search ............... 435/7.36, 7.94, 966, 435/968, 975, 18, 19, 21, 24, 29; 436/518, 532

[56] References Cited

U.S. PATENT DOCUMENTS

| | | | |
|---|---|---|---|
| 4,092,408 | 5/1978 | Litt | 436/531 |
| 4,497,899 | 2/1985 | Armstrong et al. | 436/510 |
| 4,525,452 | 6/1985 | Jones et al. | 435/29 |
| 4,663,291 | 5/1987 | Rose | 435/259 |
| 4,683,196 | 7/1987 | McLaughlin | 435/7.36 |
| 4,835,099 | 5/1989 | Mize et al. | 435/18 |

FOREIGN PATENT DOCUMENTS 8602733 5/1986 PCT Int'l Appl.
0183383 6/1986 United Kingdom.

OTHER PUBLICATIONS

Peterman et al, J. Immunol. Methods, 111:271-275 (1988).
McLean, American Biotechnology Laboratory, 10(5):58 (May 1992).
Conradie et al, J. Immunol. Methods. 59:289-299 (1983).
Lin et al. J. Immunol. Methods, 125:67-77 (1989).
Suter et al, Immunology Letters, 13:313-316 (1986).
Butler, Ed., Immunochemistry of Solid-Phase Immunoassay, CRC Press, pp. 3-14, 221-231 (1991).
Sankoili et al, "Improvement in the Antibody Binding Characteristics of Microtitre Wells by Pretreatment with Anti-IgG Fc Immunoglobulin", J. Immunol. Methods 104:191-194 (1987).
Schoenwald, E., et al, Biological Abstracts, vol. 86(2), 1988, Abstract No. 16541.
Barnes, R. C. et al, Biological Abstracts, vol. 81(3), 1986, Abstract no. 24391.
Ash, C., Chemical Abstracts, vol. 108, 1988, Abstract No. 184747b.

Primary Examiner—Esther L. Kepplinger
Assistant Examiner—Carol E. Bidwell
Attorney, Agent, or Firm—Donna R. Fugit; Richard E. Brown

[57] ABSTRACT

An assay for Chlamydia includes contacting Chlamydia organisms in a liquid with a solid support having an antispecies Fc antibody immobilized thereon and an anti-Chlamydia capture antibody. After binding of Chlamydia antigen to the capture antibody and binding of the capture antibody to the antispecies antibody on the support, a tracer including a label conjugated to a signal antibody is added. After binding of the signal antibody to the antigen, the presence of Chlamydia organisms in the liquid is detected by a signal associated with the label thereby bound to the support. The invention includes a kit of materials for performing an assay according to the method of the invention.

20 Claims, 3 Drawing Sheets

LAYERED SANDWICH ASSAY METHOD FOR CHLAMYDIA AND MATERIALS THEREFOR

This application is a continuation of application Ser. No. 07/334,255, filed Apr. 6, 1989, now abandoned.

BACKGROUND OF THE INVENTION

1. Field of the Invention

This invention relates to assay for an analyte and more particularly relates to an improved solid phase assay for Chlamydia.

2. Background of the Invention

The genus Chlamydiaceae includes two species, *Chlamydia trachomatis* and *Chlamydia psittaci*. *Chlamydia trachomatis* in its some 15 various strains is the etiologic agent for a number of human ocular and genital diseases, including trachoma, inclusion conjunctivitis, lymphogranuloma venereum, "nonspecific" or non-gonococcal urethritis and proctitis. *C. trachomatis* infection is pervasive throughout the general population. It has been estimated, for instance, that *C. trachomatis* is accountable for several million cases per year of non-gonococcal urethritis.

Since *C. trachomatis* mediated disease is widespread, a reliable, simple and inexpensive test for the organism's presence is highly desirable and of great importance so that proper treatment can be undertaken. The only serological test in current use is the microimmunofluorescence test. This test, however, requires that the strains of *C. trachomatis* be used as serological test antigen. In addition, the facilities for conducting this test are available in only a limited number of laboratories throughout the world. The test is very laborious, time consuming and difficult to perform.

Several immunoassay procedures for Chlamydia have been disclosed. PCT published application number WO 86/02733 discloses assay for various antigens, including Chlamydia which cause ocular infections. The assay includes immobilizing the antigen on a solid support by binding to a monoclonal antibody absorbed on the support, or the antigen is absorbed directly onto the solid support.

European Patent Application Number 0183383 discloses an assay for Chlamydia antigen which includes an isolation procedure in which the antigen is heated to a temperature of about 100° C. to reduce nonspecific binding, then absorbed directly onto the support.

Rose, in U.S. Pat. No. 4,663,291 discloses treating a specimen suspected of containing Chlamydia organisms with a surfactant and a metal ion to release Chlamydia antigen and assay of the antigen by known methods including immobilization of the antigen on an absorbed antibody or absorption of the antigen directly onto the support.

Armstrong et al. in U.S. Pat. No. 4,497,899, discloses an immunoassay for Chlamydia antigen in which a sample suspected of containing Chlamydia organisms is lysed to release the antigen which is absorbed directly onto a solid support.

Sankolli et al., in the *Journal of Immunological Methods* discloses precoating microtiter wells with immunoglobulins to improve the binding of antibodies thereto leading to improved reproducibility of immunoassay for estradiol carried out in the wells.

In spite of the above disclosures, there yet remains a definite need for further improvement in assay for Chlamydia. It is toward fulfillment of this need that this invention is directed.

SUMMARY OF THE INVENTION

A method for solid phase assay for Chlamydia in a body sample includes combining a liquid suspected of containing Chlamydia antigen with a solid support having an antispecies antibody immobilized thereon, an anti-Chlamydia antibody, hereinafter referred to as the capture antibody, and a tracer including a label conjugated to a second anti-Chlamydia antibody, hereinafter referred to as the signal antibody. Binding between the antispecies antibody and capture antibody, between the capture antibody and antigen and between the signal antibody and the antigen is induced, and the solid support is separated from the liquid. The separated support is examined for a signal associated with the label, the presence of label on the support indicating the presence of Chlamydia antigen in the body sample.

A preferred antigen is a lipopolysaccharide associated with the cell membrane of Chlamydia so that, in a preferred embodiment of the invention, Chlamydia organisms may be detected without prior treatment to release the antigen. A preferred label is an enzyme covalently conjugated to the signal antibody. When the label is an enzyme, the separated support may be immersed in a second liquid containing a substrate for the enzyme. Color development in the second liquid resulting from reaction of the enzyme and the substrate is indicative of the presence of Chlamydia in the body sample.

In the most preferred embodiment of the invention, Chlamydia organisms in a body sample are detected with alkaline phosphatase covalently conjugated to a monoclonal signal antibody.

The antispecies antibody which reacts with the capture antibody is preferably raised in a species different from that used to raise the capture antibody and affixed to the solid support by physical absorption.

The invention includes a kit of materials useful in performing an assay accordingly to the method of the invention.

Thus, by precoating the solid support with the antispecies antibody, the capture antibody is immobilized on the support in an orientation which presents the active binding site to the antigen. Greatly increased sensitivity in detection of Chlamydia infections in a patient is thereby provided.

DETAILED DESCRIPTION

Figure 1:
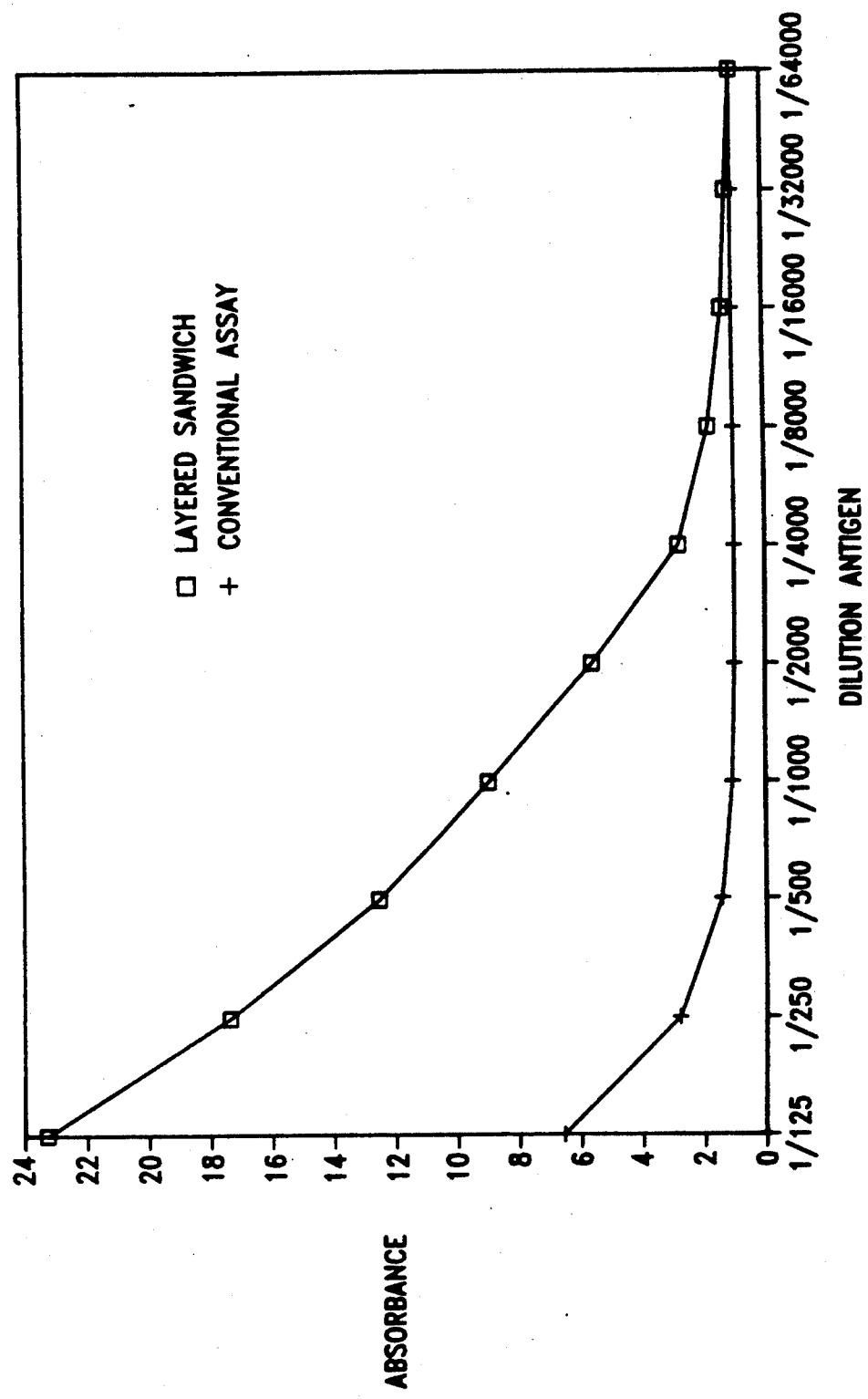
FIG. 1 shows the results of an assay for Chlamydia by the method of the invention using rabbit anti-goat antibody compared to a conventional sandwich assay.

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the invention, it has been found that polyclonal antibodies raised against Chlamydia organisms do not coat onto plastic surfaces in a random fashion as is the case with other polyclonal antibodies. It is believed, although not yet substantiated, that the Chlamydia specific antibody has an affinity for the plastic surface such that the active portion of the antibody binds to the surface and is therefore at least partially masked from the antigen. Poor results may therefore be obtained when assay for Chlamydia is performed with anti-Chlamydia antibodies immobilized directly onto the support. The present invention describes a method that orients the anti-Chlamydia antibodies so that the active portion of the antibody is exposed for binding to Chlamydia antigen and results in a much more sensitive assay than is obtained by direct attachment of the antibodies to the support The method of the invention includes at least three antibodies, the capture antibody, the antispecies antibody and the signal antibody. The capture antibody may be either polyclonal or monoclonal, preferably polyclonal, and may be raised against the antigen in any suitable animal, as for example, a rabbit, goat or mouse. The antispecies antibody is likewise preferably polyclonal, and is raised in a species different from the species used to raise the capture antibody. "Antispecies antibody" is an art term for an antibody raised in one animal against a purified antibody, or the Fc region thereof, from a different species. Thus, for example, in the present disclosure, the antispecies antibody may be a rabbit anti-goat antibody, a goat anti-rabbit antibody, a goat anti-mouse antibody and the like. Techniques for raising antibodies and antispecies antibodies are well-known to those skilled in the art, and no further details are needed for a complete understanding of the invention.

The assay of the invention may be carried out on the surface of a solid support. As known in the art, the solid support may be any support which does not substantially interfere with the assay. Exemplary of solid supports which may be used are glass and polymeric materials, such as polyethylene, polystyrene and the like. Such supports may be fabricated into any suitable shape, such as sheets, tubes, wells, or preferably, plates such as microtiter plates. A preferred solid support is a tube, preferably a plastic tube with one closed end, or most preferably, to the wells of a microtiter plate.

The antispecies antibody may be immobilized on the solid support in any suitable way, as known in the art. Immobilization may be by covalent bonding or, preferably, by absorption. Antibody absorption onto a solid support is conventional and may preferably be carried out by incubating the support and the antibody for a suitable time, generally about 10 minutes to 24 hours at a temperature of about 4°–50° C., preferably about 37° C.

Any binding sites on the support which are not filled with antispecies antibody may preferably be blocked with an inert protein, such as casein or albumin. (In the present disclosure, an inert protein is any protein capable of immobilizing on the support without substantially interacting in any way with any other assay component.) Blocking with an inert protein is conventional in the art and generally serves to substantially eliminate nonspecific binding.

The blocked support having the antispecies antibody immobilized thereon may be contacted with a solution of the capture antibody in an appropriate vehicle, preferably saline or a buffer, in order to cause binding between the antispecies antibody and the capture antibody. Binding may be induced by incubating the support and capture antibody for about 10 minutes to 24 hours at about 4° to 50° C. preferably about 1 to 2 hours at 25° to 37° C. Alternatively, capture antibody may be bound to the antispecies antibody on the support prior to or subsequent to application of the inert protein.

A sample suspected of harboring a Chlamydia infection may be taken from a patient's body by any conventional means. Preferably a swab sample is taken, most preferably a genital sample, and suspended in a liquid, such as a buffer, by agitating the swab to release the Chlamydia organisms into the buffer which may then serve as the assay liquid. It is understood, however, that, if the sample is a body fluid, it may serve as the assay liquid, or the sample may be modified in any way deemed suitable prior to binding of the antigen to the capture antibody, as described below.

Binding between Chlamydia antigen in the sample and the capture antibody bound to the antispecies antibody may be performed as described above for binding between the antispecies and capture antibodies. It is evident, however, that binding of the capture antibody and antigen may be carried out away from the support, and the bound antigen-capture antibody complex then brought into contact with the immobilized antispecies antibody on the support.

The preferred antigen of the invention is a Chlamydia cell surface lipopolysaccharide, and accordingly, the assay is preferably performed with Chlamydia cells. However, if it is desired to assay for an antigen which is not exposed on the cell surface, the cells may be pretreated to achieve greater exposure of the antigen. Any reagent or technique which alters the Chlamydia cells in a manner which renders the antigen more available for binding to the capture antibody and tracer may be used. For example, a surfactant may be used to disrupt the cells, or a conventional technique such as osmotic lysis or sonication may be used.

Antigen immobilized on the support by binding to capture antibody may be detected by any conventional procedure which includes a tracer. For example, the tracer may include the signal antibody, specific for the antigen, attached to a label. The signal antibody may be polyclonal or, preferably, monoclonal. Thus, as known in the art, the tracer may include the signal antibody conjugated to a label such as a radioactive atom, a fluorescent dye, or, preferably, to an enzyme. The radioactive atom, dye or enzyme may be encapsulated in a liposome and the liposome conjugated to the signal antibody. Methods to encapsulate labels in liposomes and to conjugate liposomes or labels to antibodies are well-known.

The antigen may be contacted with tracer to induce binding to the signal antibody either prior to, concurrent with or subsequent to binding of the antigen to the capture antibody. When all binding reactions are complete, a bound fraction including the label is immobilized on the support in proportion to the quantity of immobilized antigen. The solid support may then be separated from the liquid phase of the assay and the label on the support may be detected by a signal associated with the label to determine the presence of the antigen in the sample. If it is desired to determine the concentration of the antigen in the sample, the quantity of label on the solid support is determined by measuring the signal and comparing it to the signal obtained when a sample containing predetermined quantity of antigen is measured by the method of the invention.

If the label is a radioactive atom, the signal measured is the counts of radioactivity emitted from the solid support. If the label is a fluorescent dye, the solid support, after separation from the liquid phase may be subjected to electromagnetic energy having a wavelength within the absorption band of the dye. Absorbed energy is emitted from the dye as fluorescence, detection of which is indicative of the presence of the antigen in the sample.

The preferred label is an enzyme covalently conjugated to the signal antibody. In one embodiment of the invention, hereinafter referred to as the direct assay, the solid support, after separation, is immersed in a second liquid containing a substrate for the enzyme. The substrate is converted by the enzyme to a colored product, and detection of color is indicative of the presence of antigen in the sample. Color intensity may be measured by a colorimeter or spectrophotometer and compared to color intensity obtained when the assay is repeated with a sample containing a predetermined quantity of antigen as a measure of antigen concentration.

Any enzyme which may be conjugated to an antibody and which can convert a substrate to a colored product may serve as the label. A preferred enzyme is a peroxidase, such as horseradish peroxidase (HRP), or, most preferably, a hydrolase. A suitable hydrolase is, for example, a peptidase, esterase, such as carboxyesterase, a glycosidase, such as alactosidase or, most preferably, a phosphatase such as alkaline phosphatase.

Any substrate which reacts with the enzyme label to give a colored product may be used. Thus, if the enzyme is HRP, suitable substrates are diaminobenzidine or, preferably, ortho phenylenediamine. If the enzyme is an esterase, the substrate may be, for example, p-nitrophenyl acetate or butyrate. If the enzyme is a phosphatase such as the preferred alkaline phosphatase, suitable substrates are phosphates, such as p-nitrophenyl phosphate or indoxyl phosphate. The substrate may be present in the substrate solution at a concentration of about 0.1 to 10 mM, preferably about 1 to 5 mM. Selection of a suitable substrate and the concentration thereof to be used is well within the purview of one skilled in the art.

In general, the reaction of enzyme and substrate to form the colored product is rapid, and, in the direct assay, a time of about 1 to 30 minutes, preferably about 5 to 15 minutes is sufficient for color formation. The color forming reaction may be allowed to go for any length of time before being judged positive (color, therefore antigen present) or negative (no color, therefore no antigen). Alternatively, the reaction may be stopped at any time after combining enzyme and substrate with a stop solution. The stop solution inhibits enzyme activity and thereby freezes color development at the point of addition of the substrate solution. A suitable stop solution is, for example. 10 mM ethylenediamine tetraacetic acid in 0.2M sodium phosphate.

A preferred assay method of the invention is a dual enzyme assay carried out on the coated support having antispecies antibody, capture antibody, blocking protein and antigen bound thereto. In this embodiment of the assay method, the label may be considered to be a first enzyme which removes a blocking group from a blocked inhibitor. Suitable first enzymes are generally hydrolases, such as phosphatases, peptidases, esterases, glycosidases and the like. Exemplary of, but not limited to, suitable first enzymes are trypsin, thrombin, mammalian liver esterase, acetylcholinesterase, $\beta$-galactosidase, or most preferably, alkaline phosphatase.

The blocked inhibitor may be any material which may be converted by the first enzyme to an inhibitor of the second enzyme. The preferred blocked inhibitor has two components, the inhibitor and the blocking group and is unreactive toward the second enzyme until its blocking group is removed by the first enzyme and the inhibitor is liberated into the assay medium. Thus, the choice of the components of the blocked inhibitor depends on the first and second enzymes to be used. The blocking group should be one which can be covalently conjugated to the inhibitor by a bond which can be cleaved substantially selectively by the first enzyme, and the inhibitor component should inhibit the activity of the second enzyme while having substantially no effect on the first enzyme. Thus, the nature of the second enzyme and its substrate will be discussed prior to further description of the blocked inhibitor and the inhibitor.

The second enzyme of the dual enzyme assay is generally a hydrolase which converts the substrate to a product detectable by a signal associated with color. It is preferred that the second enzyme is substantially unreactive toward the blocked inhibitor. Suitable hydrolases are, for example, phosphatases, peptidases such as trypsin, chymotrypsin and pepsin, or preferably esterases such as acetyl cholinesterase (AChE) and butyl cholinesterase. The most preferred second enzyme is a carboxyesterase, such as pig or rabbit liver esterase (RLE) wherein the preferred substrate is an indolyl ester such as, for example, 3-indolyl acetate and 3-indolyl butyrate or a phenyl ester such as o-nitrophenyl butyrate.

As mentioned above, the first enzyme component of the tracer cleaves the blocking group from the blocked inhibitor to provide the inhibitor of the second enzyme. Suitable inhibitors and blocked enzyme inhibitors are illustrated by the general formula I set forth below, wherein the nature of group B, as described later, determines whether the compound is an inhibitor or a blocked inhibitor:

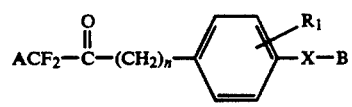
I

In formula I $R_1$ may be H, lower alkyl of 1–6 carbon atoms, branched or unbranched, nitro, alkoxy, halogen and the like; X may be O, S or $NR_2$ wherein $R_2$ may be H or lower alkyl of 1–6 carbon atoms; n may be 0–6; A may be F or $CF_3$; and B may be H, a phosphoric acid or salt, a glycosyl group, an amino acid residue, such as a lysine or arginine residue covalently conjugated to X through the amino acid carboxyl group, an acyl group of 2–4 carbon atoms such as an acetyl or butyryl group, or a peptide of the formula II

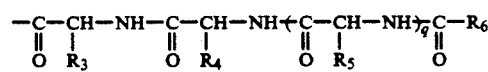

wherein $R_3$ is $(CH_2)_4NH_2$.

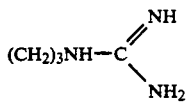

or benzyl $R_4$ and $R_5$ may be H, lower alkyl or hydroxylower alkyl of 1 to 4 carbon atoms, branched or unbranched, $CH_2COOH$ or $(CH_2)_2COOH$; $R_6$ may be lower alkyl or lower alkoxy of 1 to 4 carbon atoms, branched or unbranched, phenyl, or benzyloxy; and q may be 0-10.

When B is H, formula I represents enzyme inhibitors. When B is any group other than H, formula I represents blocked enzyme inhibitors. When B is a phosphoric acid or salt thereof, it is intended that B have the formula III

III wherein P is bonded to X and n may be as described above.

The inhibitor and blocked inhibitor in accordance with formula I may be synthesized by any sequence of conventional chemical reactions as may be envisioned by one skilled in the art. Suitable and convenient methods are given in the Examples, below. The following list of effective enzyme inhibitors is intended to be exemplary only.

Chlamydia antibody conjugated to an enzyme or it may include a second enzyme and a blocked inhibitor of the second enzyme. A substrate reactive with the enzyme or with the second enzyme may be included in the kit. Solutions and utensils useful in performing an assay according to the method of the invention may be included in the kit, such as a buffer, saline, a solution containing a predetermined quantity of antigen, containers, droppers and the like.

The following examples are included to further describe the invention but are in no way to be considered as limitative of the invention.

EXPERIMENTAL

Routine Analytical Techniques—Flash Silica gel chromatography was performed on ICN silica gel 32-63 mesh at 3-7 psi. Analytical TLC was performed on 0.25 mm 5×20 cm aluminum-backed silica gel plates from EM Scientific. Preparative TLC was performed on 2.0 mm 20×20 cm glass back silica gel plates from EM Scientific. Melting points were performed on a Thomas Hoover capillary melting point apparatus and are uncorrected. NMR spectra were recorded on an IBM WP-200SY spectrophotometer and chemical shifts are reported in ppm relative to trimethylsilane. HPLC was performed on a Waters 510 two pump system with UV detection using one of two solvent systems on a Brownlee AX- 300 7×250 mm column. (System A) initial hold for 5 minutes at 30 mM NH4OAc pH 6.5 followed by a linear gradient to 2.0M NH4OAc over a 30 minute period followed by a hold at 1.0M NH4OAc for 5 minutes. System B) used an isocratic buffer system of 30 mM NH4OAc pH 6.5 for 40 minutes. Flow rates

| Name | nmr data | $K_i$ (M) (Esterase) |
|---|---|---|
| 1. 1,1,1-trifluoro-3-(4-hydroxyphenyl)propanone | (CDCl3) - 3.91(s, 2H), 5.21(bs, 1H), 6.90(d, 2H), 7.10(d, 2H) | $2.0 \times 10^{-6}$, RLE |
| 2. 1,1,1-trifluoro-3-(3-hydroxyphenyl)-2-propanone | (CDCl3) - 4.00(s, 2H), 4.80(bs, 1H), 6.80(m, 3H), 7.30(m, 1H) | $>10^{-4}$, PLE |
| 3. 1,1,1-trifluoro-4-(4-hydroxyphenyl)-2-butanone | (CDCl3) - 2.95(m, 4H), 4.90(bs, 1H), 6.92(dd, 4H)J=4.60Hz | $2.0 \times 10^{-8}$, RLE |
| 4. 1,1,1-trifluoro-4-(3-hydroxyphenyl)-2-butanone | (CDCl3) - 2.94(t, 2H), 3.05(t, 2H), 5.70(bs, 1H), 6.80(m, 3H), 7.15(m1H) | $1.0 \times 10^{-7}$, RLE |
| 5. 1,1,1-trifluoro-5-(4-hydroxyphenyl)-2-pentanone | (CDCl3) - 1.91(t, 2H), 2.59(t, 2H), 2.68(t, 2H), 5.23(bs, 1H), 6.95(d, 2H), 7.10(d, 2H) | $1.0 \times 10^{-8}$, RLE |
| 6. 1,1,1-trifluoro-5-(3-hydroxyphenyl)-2-pentanone | (CDCl3) - 1.95(p, 2H), 2.70(t, 2H), 2.95(t, 2H), 5.40(bs, 1H), 6.70(m, 3H), 7.30(m, 1H) | $1.7 \times 10^{-7}$, RLE |
| 7. 1,1,1-trifluoro-6-(4-hydroxyphenyl)-2-hexanone | (CDCl3) - 1.63(m, 4H), 2.59(q, 2H), 2.70(q, 2H), 5.55(bs, 1H), 6.77(d, 2H) 7.02(d, 2H) | $2.0 \times 10^{-8}$, RLE |
| 8. 1,1,1,2,2-pentafluoro-5-(4-hydroxyphenyl)-3-pentanone | (CDCl3) - 2.94(m, 2H), 3.04(m, 2H), 4.75(bs, 1H), 6.90(d, 2H), 7.10(m, 2H) | $8.0 \times 10^{-7}$, RLE |

PLE, Pig Liver Esterase (E.C. 3.1.1.1)
RLE, Rabbit Liver Esterase (E.C. 3.1.1.1)

When the assay of the invention is performed by the dual enzyme format, the color forming reaction is preferably stopped as described above and is allowed to proceed for 10 to 60, preferably 20 to 40 minutes before stopping. It is understood that, in a dual enzyme assay, color development is inversely proportional to antigen concentration.

Another aspect of the invention is a kit of materials for performing the method of the invention. The kit may contain a solid support having immobilized thereon a complex of an antispecies antibody and an anti-Chlamydia antibody bound specifically to the antispecies antibody. The kit may also include an antiwere 1.0 mL/minute. Gas chromatography was performed on a H.P. 5840A Gas Chromatograph equipped with a FID and an automatic injector using a 30M DB 1 Megabore column purchased from J&W Scientific, Inc. GC conditions were as follows: A three minute hold at 100° C. followed by a 10° C./minute gradient to 250° C. followed by a 3.0 minute hold at 250° C. at 16.0 mL/minute flow rate.

Inhibition constants were measured in 50 mM Tris pH=8.0. Enzyme and inhibitor were incubated at ambient temperature for 20 minutes. Substrate for the enzyme was then added and the rate of hydrolysis was followed spectrophotometrically. The substrate for PLE and RLE was o-nitro-phenylbutrate and for AChE was acetyl thiocholine and Ellman's reagent.

EXAMPLE I

Diammonium [4-(3-oxo-4,4,4-trifluorobutyl)phenyl] phosphate

A. Preparation of Ethyl 2-(4-methoxybenzyl)-3-oxo-4,4,4-trifluorobutanoate

A 1 L four neck round bottom flask, fitted with reflux condenser, dropping funnel, argon inlet, and magnetic stirrer was charged with 7.17 g (0.149 mol) of a 50% (w/v) oil dispersion of sodium hydride and 300 mL of dry ethyl ether. Absolute ethanol (9.0 mL) was slowly added to the stirred solution. After the evolution of hydrogen stopped, a mixture of 25 g (0.136 mol) of ethyl 4,4,4-trifluoroacetoacetate and 21.3 (0.136 mol) of 4-methoxybenzyl chloride was added over a 1 hour period. The resulting mixture was refluxed overnight, cooled, extracted with water, 1N hydrochloric acid, dried over anhydrous magnesium sulfate and rotary-evaporated under reduced pressure. The crude reaction mixture (33.5 was chromatographed on a 60 mm xx 300 mm silica gel column with ethyl acetate/hexane (25/75). Similar fractions were combined and gave 9.4 g (23%) of the (spectroscopically complex) product as an oil. NMR(CDCl3): 1.26(m,3H), 3.77(s,3H), 4.12(m,2H), 7.08(m,2H).

B. Preparation of 1,1,1-trifluoro-4-(4-hydroxyphenyl)-butan-2-one

A 100 mL round bottom flask, fitted with reflux condenser, magnetic stirrer and argon inlet was charged with 2.05 g (6.7 mmol) of ethyl 2-(4-methoxybenzyl)-3-oxo-4,4,4-trifluorobutanoate (I), 20 mL of 31% (w/v) hydrogen bromide in acetic acid, and 10 mL of water. This mixture was heated overnight at 120° C., cooled, concentrated under reduced pressure and partitioned between dichloromethane and water. The organic layer was extracted sequentially with aqueous bisulfite, and saturated sodium bicarbonate, and then dried over anhydrous magnesium sulfate. Solvent was removed under reduced pressure. The crude reaction mixture was chromatographed on a 50 mm×300 mm silica gel column with ethyl acetate/hexane (50/50). Similar fractions were combined and the solvent was removed under reduced pressure to yield 600 mg (41%) as a clear oil. NMR(CDCl3): 2.95(m,4H), 5.40(bs, 1H), 6.93(dd,4H) J=4, 60 Hz.

C. Preparation of diethyl [4-(3-oxo-4,4,4-trifluorobutyl)phenyl] phosphate

A 10 mL round bottom flask, fitted with argon inlet and magnetic stirrer was charged with 400 mg (1.8 mmol) of 1,1,1-trifluoro-4-(4-hydroxyphenyl)butan-2-one, 400 mg (2.3 mmol) of diethyl chlorophosphate, 0.15 mL of dry pyridine and 5 mL of dichloromethane. The reaction mixture was stirred overnight at ambient temperature, filtered to remove pyridinium hydrochloride, extracted with 0.2N hydrochloric acid, extracted with water, and dried over anhydrous magnesium sulfate. Solvent removal under reduced pressure afforded a crude yield of 600 mg of a brown oil. Two hundred mg (31%) of a clear oil was isolated from a preparative TLC plate developed with ethyl acetate/hexane (50/50). NMR(CDCl3): 1.50(m6H), 3.0(m,4H), 4.20(m,4H), 7.15(s,4H).

D. Preparation of diammonium [4-(3-oxo-4,4,4-trifluorobutyl)phenyl] phosphate

A 25 mL one neck round bottom flask, fitted with argon inlet and magnetic stirrer was charged with 5.0 mL of dichloromethane, 140 mg (0.40 mmol) of diethyl [4-(3-oxo-4,4,4-trifluorobutyl)phenyl] phosphate (III) and 2.0 mL of bromotrimethylsilane. After stirring this mixture for 3 hours at ambient temperature, 10 mL of methanol was added and the volatile materials were removed under reduced pressure. The residue was dissolved in water and adjusted to pH 7.0 with 1.0N sodium hydroxide. The aqueous solution was extracted with diethyl ether and lyophilized to give 190 mg of a white solid. This material was dissolved in 10 mL of water, and purified by anion exchange HPLC. Gradient conditions: initial hold for 5 minutes at 20 mM ammonium acetate, pH 6.5; followed by a linear ramp to 1.0M ammonium acetate over a 20 minute period; followed by a hold at 1.0M ammonium acetate for 15 minutes. At a flow rate of 2.5 mL/min, the product eluted at approximately 32 minutes. Column capacity was 20 mg. Product fractions from several HPLC runs were pooled and lyophilized to yield 50 mg (37%). mp 235°-240° C. NMR (D20): 1.90(m,2H), 2.56(m,2H), 4.65(s, DOH), 6.88(dd,4H) J=6, 82 Hz.

EXAMPLE II

This example compares a dual enzyme sandwich assay for Chlamydia (referred to as the conventional assay) with the dual enzyme layered sandwich method of the invention. Both assays used a rabbit polyclonal anti-Chlamydia capture antibody. For the conventional assay, the capture antibody was absorbed into wells of a microtiter tray. For the layered sandwich assay of the invention, a goat anti-rabbit $F_c$ antibody (antispecies antibody) was first absorbed in the wells of the tray.

Materials

1. Coating Buffer=63 mM sodium carbonate, 20 mM EDTA, pH 9.5
2. Wash/Block Buffer=10mM Tris, 2% casein hammarsten grade, 100 mM NaCl, pH 7.6
3. Specimen Dilution Buffer=10 mM Tris, 10 mM EDTA, 1 mM EGTA, 0.1% bovine serum albumin, pH 7.4
4. Dual Enzyme Detection System Reagents
   (a) Phosphorylated blocked esterase inhibitor, disodium [4-(3-oxo-4,4,4-trifluorobutyl)phenyl] phosphate=BI, stock solution 5 mM in 50 mM diethanolamine pH 9.0, stored at −70° C.
   (b) Rabbit liver esterase (RLE) 1.0 mg/ml stock solution in 50 mM Tris-HCl pH 7.5.
   (c) DEOA Buffer—50 mM diethanolamine, pH 9.0, 0.5 mM $MgCl_2$.
   (d) RLE & BI Working Dilution 0.4 µg/ml rabbit liver esterase (RLE), 0.1 mg/ml ovalbumin, 0.15 mM BI in DEOA buffer. This solution was prepared immediately before needed from individual stock solutions of RLE and BI.
   (e) Chromogen Stock—100 mM o-nitrophenyl butyrate (ONPB) in dimethylsulfoxide (DMSO).
   (f) Dilution Chromogen—1.2 mM ONPB, 50 mM Tris-HCl, pH 7.5. Freshly prepared before use.

Method for Conventional Sandwich Assay

1. Capture Antibody Adsorption—Rabbit anti-Chlamydia antibody was adsorbed to wells of a microtiter plate by incubation of 100 µl solution containing 50 µg/ml antibody in coating buffer for 1 hour at 37° C.
2. Washing/Blocking—Excess protein binding sites were blocked and nonadsorbed antibody was removed by aspirating and then washing the wells of the microtiter plate 3 times with 200 μl/well wash/block buffer and aspirating contents.

3. Antigen Binding—*Chlamydia trachomatis* elementary bodies were diluted in specimen dilution buffer. One hundred μl of the appropriate dilution was added per well and incubated at 37° C. for 1 hour.

4. Washing/Blocking—Step 2 as described above was repeated.

5. Tracer Binding—An anti-Chlamydia monoclonal antibody alkaline phosphatase conjugate was diluted to 0.2 μg/ml in wash/block buffer. One hundred μl was added per well and the binding incubation was for 1 hour at 37° C.

6. Washing/Blocking—Step 2 as described above was repeated.

7. Detection of bound tracer by dual enzyme (a) Seventy-five μl RLE+BI solution were added per well and incubation for 20 minutes at room temperature was carried out.

(b) Seventy five μl working chromogen dilution were added per well and incubation for 10 minutes was carried out.

(c) Absorbance was read at 414 nm and divided into the zero signal at 414 nm to give a relative signal.

Method for Layered Sandwich Assay

1. Goat—Anti-Rabbit $F_c$ Adsorption—Goat anti-rabbit $F_c$ antibody was adsorbed to the wells of the microtiter plate by incubating 100 μl/well of a 10 μg/ml solution in coating buffer for 1 hour at 37° C.

2. Washing/Blocking—Identical to Step 2 of the conventional assay.

3. Capture Antibody Binding—Rabbit anti-Chlamydia antibody was diluted into wash/block buffer to 50 μg/ml. One hundred μl was added per well and the binding incubation was for 1 hour at 37° C.

4. Washing/Blocking—Identical to Step 2.

5. Subsequent steps for antigen binding through detection were identical to Steps 3-7 of the conventional assay.

The results of this experiment are shown in FIG. 1.

EXAMPLE III

Figure 2:
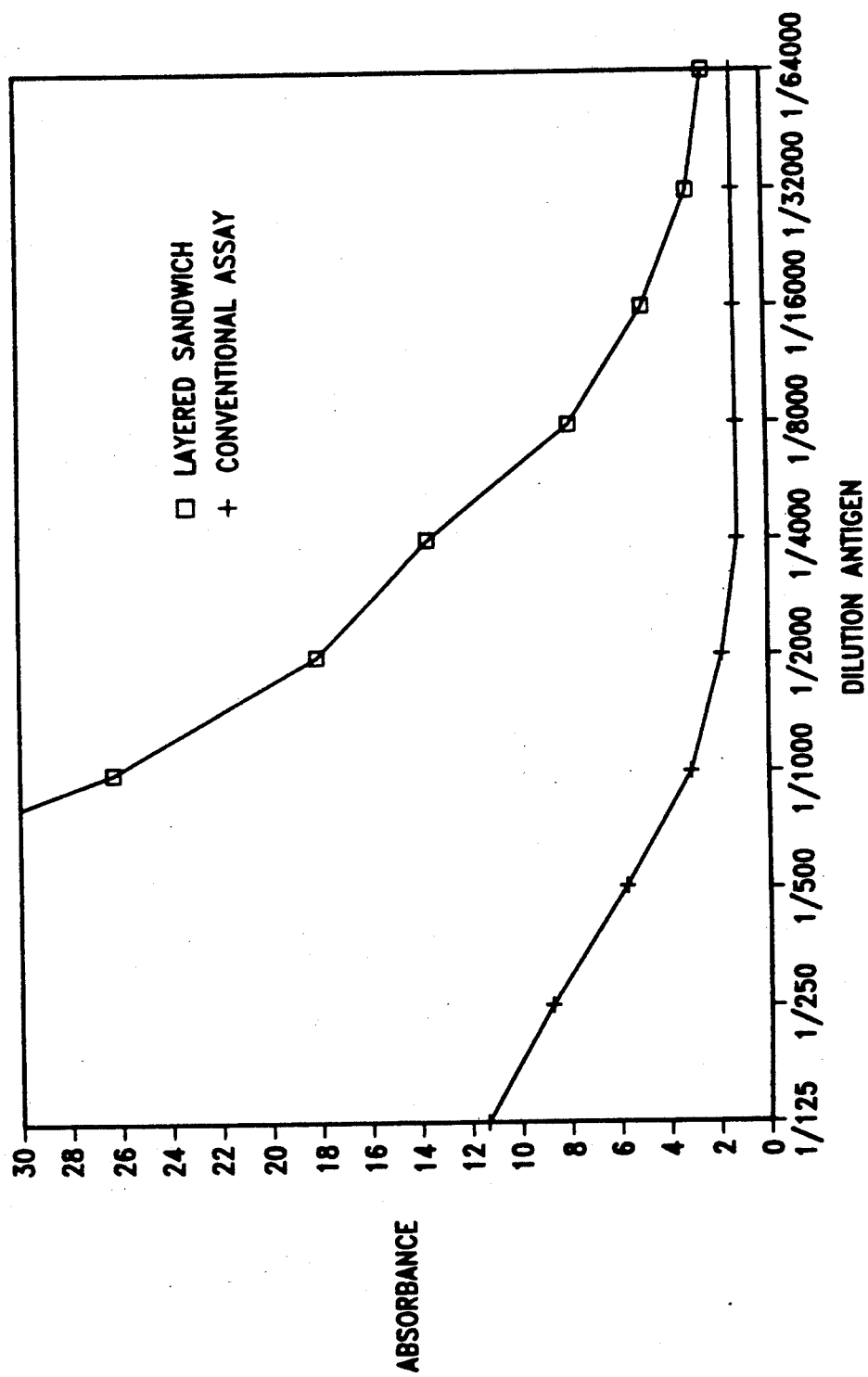
FIG. 2 shows the results of an assay for Chlamydia by the method of the invention using goat anti-rabbit antibody compared to a conventional sandwich assay.

This example again compares the conventional sandwich and layered sandwich Chlamydia assays except both assays use a goat anti-Chlamydia antibody to specifically bind Chlamydia antigen. The goat anti-Chlamydia antibody incubations were at 10 μg/ml. The layered sandwich assay was performed using a precoat, rabbit anti-goat $F_c$ adsorption at 0.5 μg/ml. The tracer was diluted in wash/block buffer that contained 0.5 mg/ml normal mouse IgG and 25 μg/ml normal goat IgG. These additions eliminated nonspecific binding of the tracer. The protocol was otherwise identical to that used in Example I. The improved assay provides a 16 to 32 fold increase in sensitivity for antigen detection as shown in FIG. 2.

This example demonstrates that the method of the invention is general for Chlamydia antigen detection for an assay using an anti-Chlamydia antibody to specifically bind antigen.

EXAMPLE IV

In the same way as described in Example III, the conventional and layered sandwich assays were performed for RSV antigen using goat anti-RSV antibody for specific antigen capture.

Figure 3:
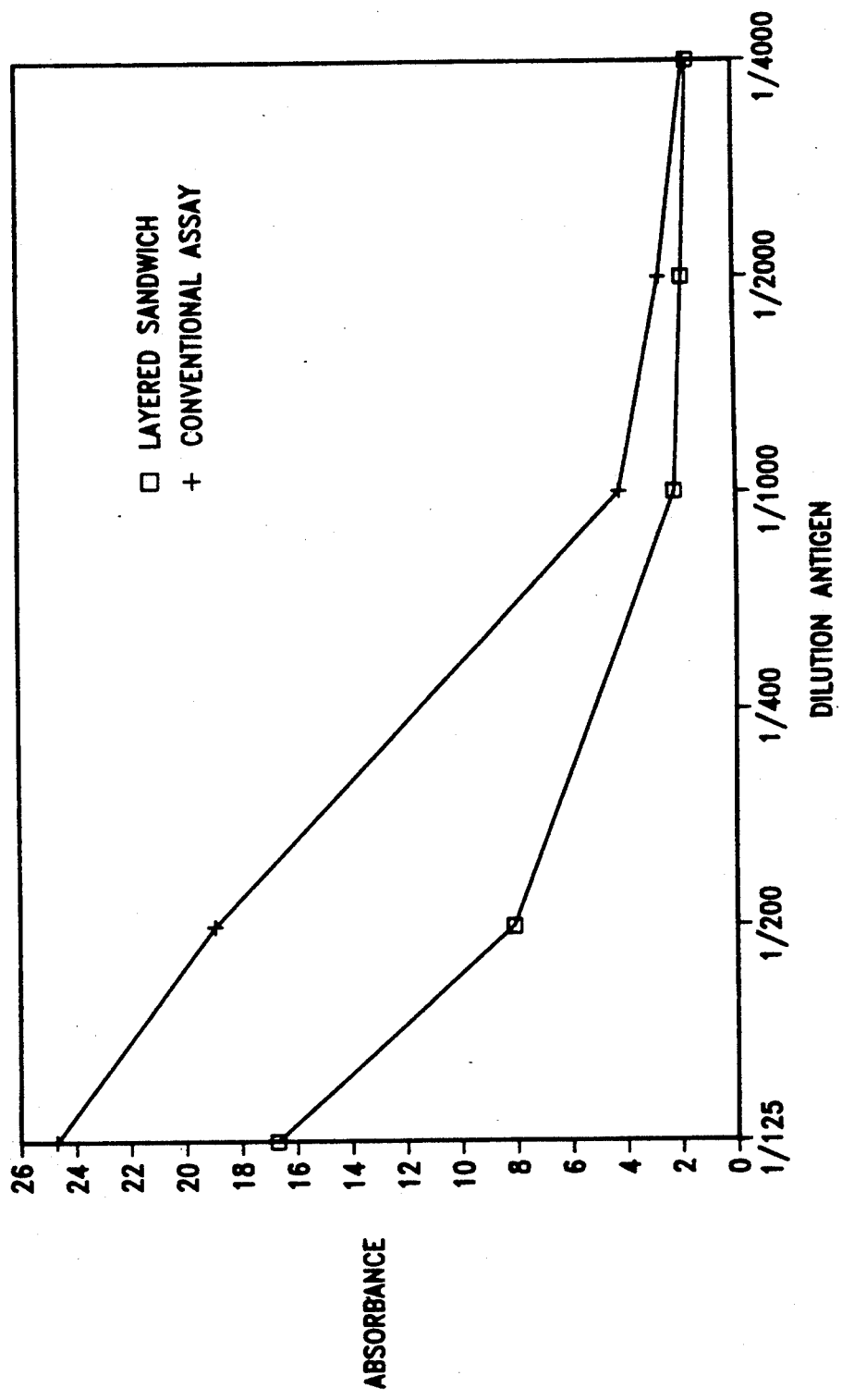
FIG. 3 shows the results of an assay for Respiratory Syncytial Virus (RSV) by the method of the invention using goat anti-RSV antibody compared to a conventional sandwich assay.

The results of this experiment, shown in FIG. 3, demonstrate that the method of the invention, while unexpectedly beneficial in assay of Chlamydia antigen, decreases slightly the sensitivity for detection of RSV antigen.

Thus, the invention provides an improved assay for Chlamydia which includes an antispecies antibody immobilized on a solid support which binds to the anti-Chlamydia antibody in such a way that the active site of the anti-Chlamydia antibody is exposed for high sensitivity binding to Chlamydia antigen.

What is claimed is:

1. A method for detecting Chlamydia antigen comprising:

a) combining a solid support having an antispecies Fc antibody immobilized thereon, a capture antibody, a sample suspected of containing a Chlamydia lipopolysaccharide cell surface antigen and a tracer comprising a signal antibody conjugated to a first enzyme whereby said capture antibody binds to said antispecies antibody, said antigen binds to said capture antibody and said signal antibody binds to said antigen to give a bound fraction containing signal antibody on said support;

b) contacting said bound support having bound signal antibody thereon with a hydrolase, a blocked fluoroketone and a substrate for said hydrolase, said first enzyme removing the blocking group from said blocked fluoroketone to a fluoroketone, said fluoroketone inhibiting conversion of said substrate to a product by said hydrolase; and c) detecting the presence of Chlamydia antigen in said sample by inhibition of the appearance of color associated with said product.

2. The method of claim 1 further comprising determining the concentration of said Chlamydia antigen in said liquid by comparing the magnitude of said color with the magnitude of color established for a known quantity of the antigen.

3. The method of claim 1 wherein said first enzyme is selected from the group consisting of a peptidase, esterase, phosphatase and glycosidase.

4. The method of claim 1 wherein said signal antibody is monoclonal.

5. The method of claim 1 wherein substantially all binding sites of said support not filled by said antispecies Fc antibody are filled with a protein which is inert to other components of the assay.

6. The method of claim 1 wherein said hydrolase is selected from the group consisting of a phosphatase, peptidase and esterase.

7. The method of claim 1 wherein said substrate is selected from the group consisting of 3-indolylacetate, 3-indolyl butyrate and ortho nitrophenyl butyrate.

8. A method for detecting Chlamydia antigen comprising:

a) combining a solid support having an antispecies Fc antibody immobilized thereon, a capture antibody, a sample suspected of containing Chlamydia antigen and a tracer comprising a signal antibody conjugated to a label whereby said capture antibody binds to said antispecies Fc antibody, said antigen binds to said capture antibody and said signal antibody binds to said antigen to give a bound fraction including said label on said support;

b) providing signal means to relate the quantity of label on said support to the quantity of antigen in said sample; and c) detecting said antigen by a signal proportional to the quantity of said label bound to said support.

9. The method of claim 8 wherein said label is selected from the group consisting of a radioactive atom, a fluorescent dye and an enzyme.

10. The method of claim 9 wherein said label is a radioactive atom and said detecting is performed by measuring radioactive counts from label bound to said support.

11. The method of claim 9 wherein said label is a fluorescent dye, and said detecting is performed by subjecting said support to excitation light and measuring fluorescence from label bound to said support.

12. The method of claim 9 wherein said label is an enzyme and said detecting is performed by contacting enzyme bound to said support with a substrate therefor and detecting the appearance of color.

13. A method for detecting Chlamydia organisms comprising:
   a) contacting a first liquid suspected of containing Chlamydia organisms with a solid support having immobilized thereon a bound complex of an antispecies Fc antibody and a capture antibody whereby said organisms bind to said capture antibody to give bound organisms on said support;
   b) separating said support having bound organisms thereon from said first liquid;
   c) adding to said support a second liquid containing a tracer comprising a monoclonal antibody conjugated to alkaline phosphatase, said monoclonal antibody binding to said organisms on said support;
   d) separating said support having bound tracer thereon from said second liquid;
   e) contacting said support with a third liquid containing carboxyesterase, a substrate reactive therewith and a blocked fluoroketone, said phosphatase removing the blocking group from said blocked fluoroketone to give a fluoroketone, said fluoroketone inhibiting conversion of said substrate to a product by said carboxyesterase; and
   f) detecting the presence of Chlamydia organisms in said first liquid by inhibition of the appearance of color in said second liquid associated with said product.

14. A kit of materials for performing an assay for Chlamydia comprising a solid support having an antispecies Fc antibody immobilized thereon, and an anti-Chlamydia capture antibody, an anti-Chlamydia signal antibody conjugated to an enzyme and a substrate reactive with said enzyme.

15. The kit of claim 14 wherein said capture antibody is bound to said immobilized antispecies Fc antibody.

16. The kit of claim 14 wherein said substrate is a blocked fluoroketone which reacts with said enzyme to give a fluoroketone.

17. The kit of claim 16 further comprising a hydrolase subject to inhibition by said fluoroketone and a substrate for said hydrolase.

18. The kit of claim 14 wherein said substrate reacts with said enzyme to give a colored : product.

19. The kit of claim 14 wherein said solid support has an inert protein immobilized in substantially all binding sites of said support except those binding sites occupied by said complex.

20. The kit of claim 14 further comprising one or more solutions containing a predetermined quantity of Chlamydia antigen.

* * * * *